United States Patent
Novak et al.

(10) Patent No.: US 6,983,063 B1
(45) Date of Patent: Jan. 3, 2006

(54) COMPUTER-AIDED DIAGNOSIS METHOD FOR AIDING DIAGNOSIS OF THREE DIMENSIONAL DIGITAL IMAGE DATA

(75) Inventors: Carol Novak, Newtown, PA (US); Jianzhong Qian, Princeton, NJ (US); Aaron Bobick, Atlanta, GA (US)

(73) Assignee: Siemens Corporate Research, Inc., Princeton, NJ (US)

( * ) Notice: Subject to any disclaimer, the term of this patent is extended or adjusted under 35 U.S.C. 154(b) by 717 days.

(21) Appl. No.: 09/606,564

(22) Filed: Jun. 29, 2000

(51) Int. Cl.
*G06K 9/00* (2006.01)

(52) U.S. Cl. .................................. 382/131
(58) Field of Classification Search ........ 382/128–132, 382/154, 282, 285, 289
See application file for complete search history.

(56) References Cited

U.S. PATENT DOCUMENTS

| | | | | |
|---|---|---|---|---|
| 4,674,046 A | * | 6/1987 | Ozeki et al. ............... | 382/131 |
| 4,907,156 A | | 3/1990 | Doi et al. .................... | 364/413 |
| 5,459,536 A | | 10/1995 | Shalon et al. ............... | 351/226 |
| 5,491,627 A | | 2/1996 | Zhang et al. ............ | 364/413.2 |
| 5,579,360 A | | 11/1996 | Abdel-Mottaleb ........... | 378/37 |
| 5,699,082 A | | 12/1997 | Marks et al. ................ | 345/157 |
| 5,724,978 A | * | 3/1998 | Tenhoff ....................... | 600/467 |
| 5,768,406 A | | 6/1998 | Abdel-Mottaleb .......... | 382/132 |
| 5,815,591 A | | 9/1998 | Rochrig et al. ............. | 382/130 |
| 5,838,815 A | | 11/1998 | Gur et al. .................... | 382/128 |
| 5,842,473 A | * | 12/1998 | Fenster et al. .............. | 600/445 |
| 5,970,115 A | | 10/1999 | Colbeth et al. ............... | 378/62 |
| 5,970,164 A | | 10/1999 | Bamberger et al. ......... | 382/132 |
| 6,075,878 A | | 6/2000 | Yoshida et al. ............. | 382/132 |
| 6,102,861 A | * | 8/2000 | Avila et al. .................. | 600/443 |
| 6,392,646 B1 | * | 5/2002 | Yamrom et al. ............ | 345/420 |
| 6,450,978 B1 | * | 9/2002 | Brosseau et al. ........... | 600/595 |
| 6,461,298 B1 | * | 10/2002 | Fenster et al. .............. | 600/437 |

FOREIGN PATENT DOCUMENTS

EP         0 487 110         6/1999

* cited by examiner

Primary Examiner—Jose L. Couso
Assistant Examiner—Tom Y. Lu
(74) Attorney, Agent, or Firm—Donald B. Paschborg; Michele L. Conover (57) ABSTRACT

There is provided a computer-assisted diagnosis method for assisting diagnosis of three-dimensional digital image data. The method includes the step of receiving indicia identifying at least one region of interest in a digital medical image. Three-dimensional objects within the at least one region of interest are identified. For a given three-dimensional (3D) object within the at least one region (ROI), an extent, a centroid, and a local spinning axis of the given object are determined. Moreover, a local spinning plane is determined for the given object, the local spinning plane being centered at the centroid and the local spinning axis. The local spinning plane is rotated at least a portion of 360 degrees. The rotating step includes the step of creating a view of the given object at predefined increments of rotation, so as to result in a plurality of views of the given object.

24 Claims, 6 Drawing Sheets

COMPUTER-AIDED DIAGNOSIS METHOD FOR AIDING DIAGNOSIS OF THREE DIMENSIONAL DIGITAL IMAGE DATA

BACKGROUND

1. Technical Field

The present invention relates generally to computer-aided diagnosis (CADx) and, in particular, to a computer-aided diagnosis (CADx) method for aiding diagnosis of three-dimensional digital image data.

2. Background Description

Computer-assisted diagnosis is an important technology in many clinical applications. In current clinical practice, cancer or other diseases may be missed during a physician's un-aided examination of medical image data, in part because of the large volume of data. This is particularly a problem for screening applications, since there is generally little time to devote to the examination of each patient's data, and the entire range of the data must be examined to make sure it is free from disease. Computer analysis that is performed silently in the background can greatly aid physicians in their work.

New technologies that offer three-dimensional (3D) scans of the human body, such as Magnetic Resonance Imaging (MRI) and Computed Tomography (CT), offer tremendous opportunities for improved detection of disease. However, the change from two dimensions to three means that there is a much larger amount of data for the physician to examine. Thus, the assistance of computer analysis becomes even more important.

The computer screen can only provide a two-dimensional (2D) view of a three-dimensional data set. There are many different approaches to presenting two-dimensional representations of such data, Traditional volume rendering algorithms sometimes produce satisfactory results, but they require pre-set thresholds to determine what types of tissue will be drawn as transparent and what types will be drawn as opaque. For complex anatomical structures, the volume rendering may be too cluttered for the physician to form a mental model of the underlying three-dimensional structure of the data, and how it corresponds to normal and abnormal anatomical structure. It would be useful for a CADx system to provide a visualization that helps the physician quickly build up the model, and easily distinguish abnormal structures from normal ones.

Unfortunately, many current CADx systems are not readily accepted by physicians, because their aid is seen as more of a distraction than a help. Many such systems present the results of the computer's diagnosis to the physician by marks, such as a red circle or arrow on the softcopy, which some physicians feel can create a bias in their interpretation of the data. Furthermore, many systems are perceived as a "black box"; that is, the physicians feel that they do not have any understanding of how the systems work and how they generate their diagnosis.

It would be more desirable to integrate physician's knowledge into the CADx process seamlessly, and without introducing marks onto the soft-copy that may be distracting or annoying to physicians.

SUMMARY OF THE INVENTION

The present invention is directed to a computer-aided diagnosis (CADx) method for aiding diagnosis of three-dimensional digital image data. The invention integrates a physician's knowledge into the computer-aided diagnosis process seamlessly, performs diagnostic computation accordingly, and then provides a novel presentation of the data that aids the physician in understanding the data.

In a first aspect of the invention, there is provided a computer-assisted diagnosis method for assisting diagnosis of three-dimensional digital image data. The method includes the step of receiving indicia identifying at least one region of interest in a digital medical image. Three-dimensional objects within the at least one region of interest are identified. For a given three-dimensional (3D) object within the at least one region (ROI), an extent, a centroid, and a local spinning axis of the given object are determined. Moreover, a local spinning plane is determined for the given object, the local spinning plane being centered at the centroid and the local spinning axis. The local spinning plane is rotated at least a portion of 360 degrees. The rotating step includes the step of creating a view of the given object at predefined increments of rotation, so as to result in a plurality of views of the given object.

In a second aspect of the invention, the step of determining the extent of the given object includes the step of examining connected voxels within a predefined volume on adjacent tomographic slices.

In a third aspect of the invention, the local spinning plane is initially oriented at a same angle as a current two-dimensional view of the three-dimensional digital image data.

In a fourth aspect of the invention, the step of providing the plurality of views of the given object further includes the step of providing a plurality of views of areas surrounding the given object.

In a fifth aspect of the invention, the indicia is provided from a user through one of a mouse and an eye tracking device.

In a sixth aspect of the invention, the providing step further comprises the step of determining at least one of a volume, a geometrical location, and a center of mass of the given object.

In a seventh aspect of the invention, the providing step further comprises the step of determining one of a circularity and a sphericity of the given object.

In an eighth aspect of the invention, the providing step further comprises the step of determining a mean, a variance, and a min/max of intensity values within the given object.

In a ninth aspect of the invention, the providing step further comprises the step of determining a texture, a surface smoothness, and regularity measures of the given object.

In a tenth aspect of the invention, the providing step further comprises the step of determining two-dimensional and three-dimensional shape measures of the given object.

In an eleventh aspect of the invention, the method further includes the step of storing results from the providing step in a table for comparison with at least one of preceding or succeeding scans of a same patient.

In a twelfth aspect of the invention, the method further includes the step of storing a confidence value in the table that indicates an estimate of a clinical relevance of the given object.

In a thirteenth aspect of the invention, the method further includes the steps of setting thresholds for particular features of particular objects that represent whether the particular objects are abnormal, and identifying a given object that exceeds a given threshold.

These and other aspects, features and advantages of the present invention will become apparent from the following detailed description of preferred embodiments, which is to be read in connection with the accompanying drawings.

DETAILED DESCRIPTION OF PREFERRED EMBODIMENTS

The present invention is directed to a computer-aided diagnosis (CADx) method for aiding diagnosis of three-dimensional digital image data. It is to be appreciated that the invention may be used to aid diagnosis of any abnormality in any part of the body which is represented in a digital image.

Figure 1:
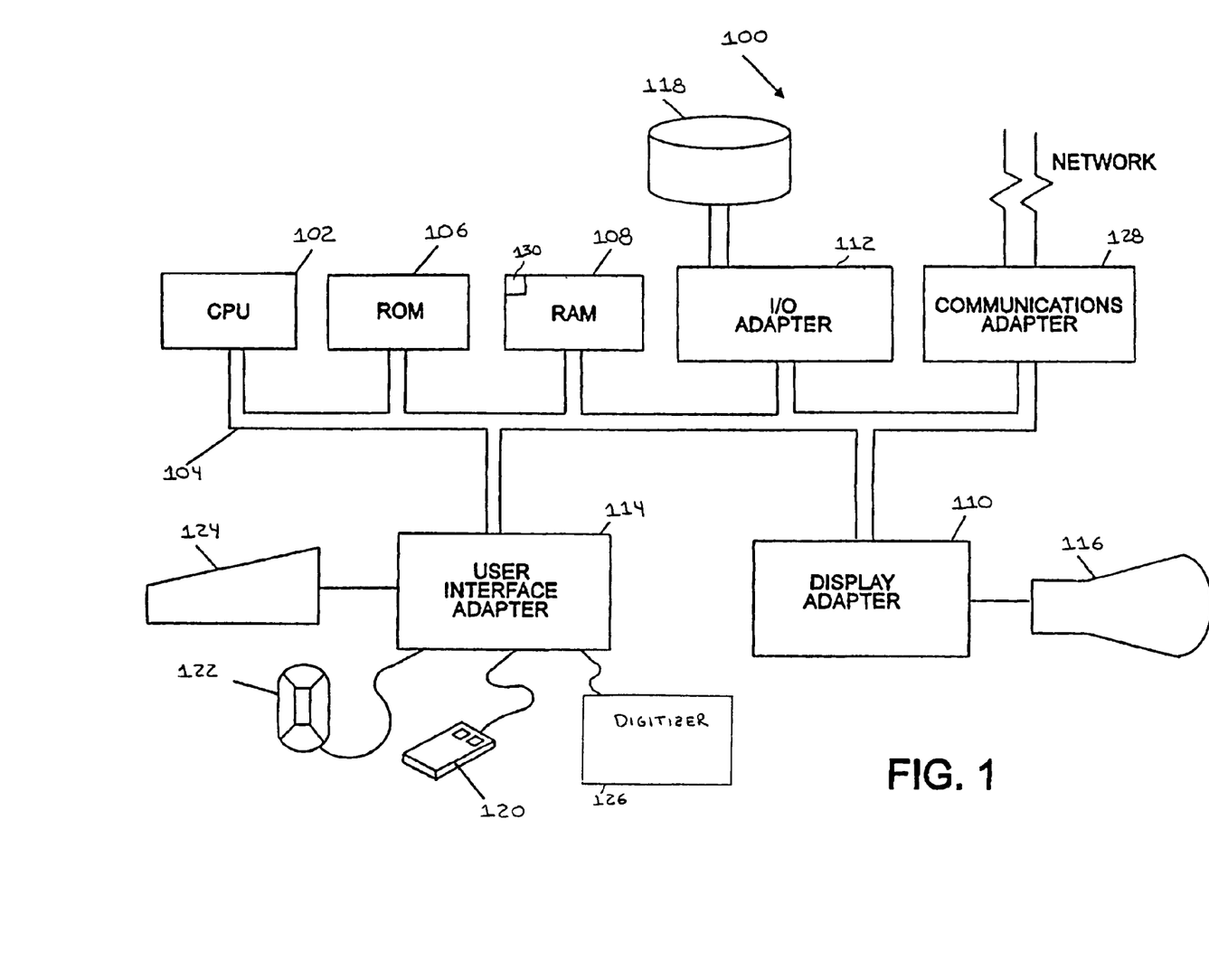
FIG. 1 is a block diagram of a computer processing system to which the present invention may be applied, according to an embodiment of the present invention.

FIG. 1 is a block diagram of a computer processing system to which the present invention may be applied, according to an embodiment of the present invention. The system 100 includes at least one processor (CPU) 102 operatively coupled to other components via a system bus 104. A read only memory (ROM) 106, a random access memory (RAM) 108, a display adapter 110, an I/O adapter 112, and a user interface adapter 114 are operatively coupled to system bus 104.

A display device 116 is operatively coupled to system bus 104 by display adapter 110. A disk storage device (e.g., a magnetic or optical disk storage device) 118 is operatively couple to system bus 104 by I/O adapter 112.

A mouse 120 and eye tracking device 122 are operatively coupled to system bus 104 by user interface adapter 114. The mouse 120 and eye tracking device 122 are used to aid in the selection of suspicious regions in a digital medical image. A keyboard 124 may also be operatively coupled to system bus 104 by user interface adapter 114. The keyboard may be used to input and output information to and from CAD system 100.

The CAD system 100 may also include a digitizer 126 operatively coupled to system bus 104 by user interface adapter 114 for digitizing a developed x-ray. Alternatively, digitizer 126 may be omitted, in which case a digital image may be input to system 100 from a network via a communications adapter 128 operatively coupled to system bus 104.

Figure 2:
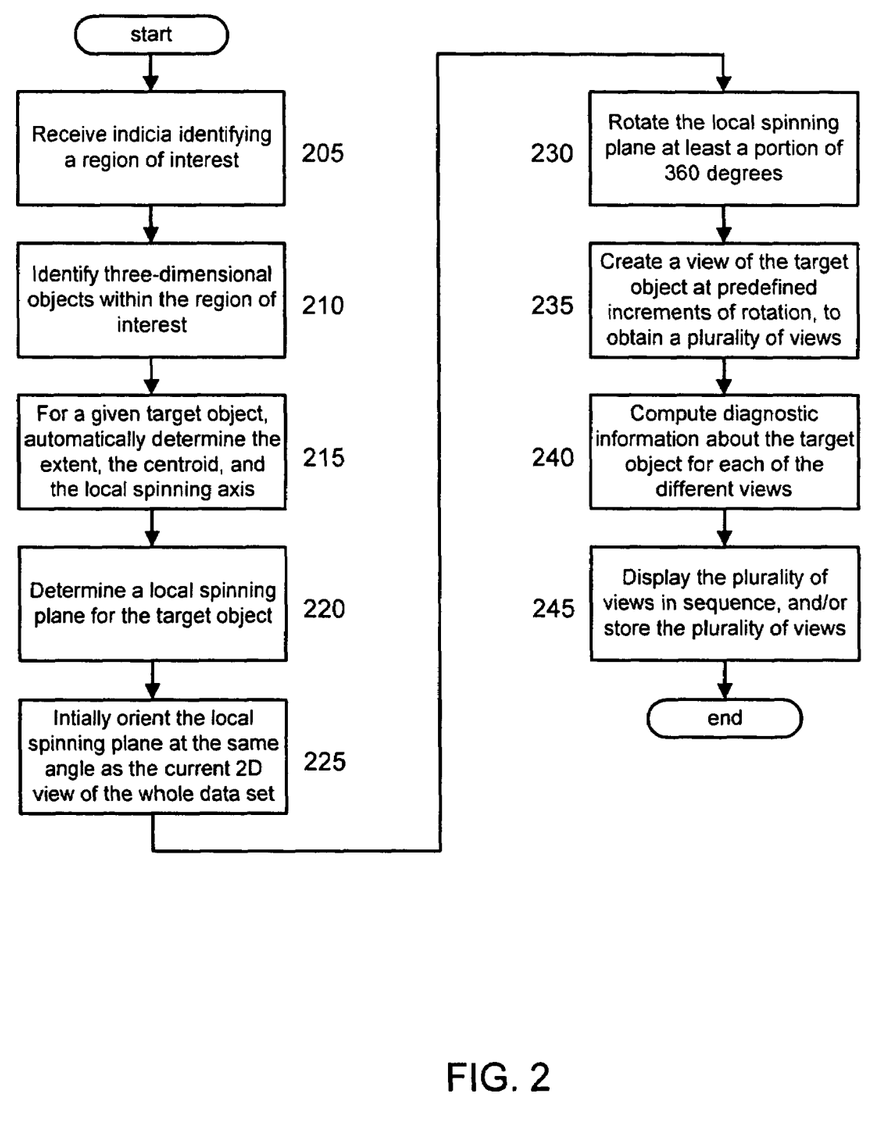
FIG. 2 is a flow diagram illustrating a computer-aided diagnosis (CADx) method for aiding diagnosis of three-dimensional digital image data, according to an illustrative embodiment of the present invention.

FIG. 2 is a flow diagram illustrating a computer-assisted diagnosis method for assisting diagnosis of three-dimensional digital image data, according to an illustrative embodiment of the present invention.

Indicia identifying a region of interest in a digital medical image is received (step 205). Step 205 is also referred to herein as "click-on" or "focus-on". In this step, the physician examines two-dimensional views of the three-dimensional data in the usual clinical way. The physician then defines the region of interest (ROI), by either clicking on the suspicious region using mouse 120, or by using other devices such as, for example, wireless eye-tracking device 122. The ROI may also be automatically detected and suggested by a computer method. It is to be appreciated that the preceding examples of how a region of interest is identified are merely illustrative and, thus, other ways of accomplishing the same may be readily contemplated by one of ordinary skill in the related art, while maintaining the spirit and scope of the invention.

Three-dimensional objects within the region of interest are automatically identified (step 210). Step 210 is also referred to herein as "center-in". In this step, once the ROI is selected by the physician (at step 205), three-dimensional objects are automatically found, if present, within the ROI. This object is known as the target object (or the given object).

To automatically find a target object, the volume of the medical image data immediately surrounding and including the region of interest (ROI) is searched according to standard search techniques. The extent of the search is defined by a threshold that is adaptive to its local maximum intensity value within the ROI. An object is detected when a voxel in the search area has a value which indicates that it corresponds to tissue, such as blood, fat, or bone, rather than air. Other 3D morphological operations can also be used to find the 3D object. Given the teachings of the present invention provided herein, one of ordinary skill in the related art will contemplate these and other ways in which target objects can be automatically identified, while maintaining the spirit and scope of the invention.

For a given (three-dimensional) target object within the region of interest, an extent, a centroid, and a local spinning axis of the target object are automatically determined (step 215). The extent of the target object is determined, by examining connected voxels within a predefined volume on the adjacent topographic slices.

Steps 220 through 245 are referred to herein as "fly around". For these steps, upon the physician's request for further examination of the target object, the three-dimensional volume of data surrounding the object is displayed for the physician to simulate how it would appear if the doctor could look all the way around the object.

At step 220, a local spinning plane is determined for the target object. The local spinning plane is centered at the centroid and the local spinning axis determined at step 215. The local spinning plane shows a small window of detail around the target object.

The local spinning plane is initially oriented at the same angle as the current two-dimensional view of the whole data set (step 225). The local spinning plane is then rotated (spun) 360 degrees (or a portion thereof) (step 230). During the spinning of the local spinning plane, a view of the target object is created at predefined increments of rotation, so as to result in a plurality of views of the target object (step 235). Moreover, during the spinning of the local spinning plane, diagnostic information is computed about the target object for each of the different views (step 240).

The different views are displayed in sequence, giving rise to a short "movie" or cine loop that simulates what it would look like to fly around the object (step 245). It is to be appreciated that, at step 240, the views may be stored in place of, or in addition to, displaying the views to the physician. If the views are stored, then they may be later retrieved for subsequent viewing and/or analysis.

The advantage of the "spinning plane" view is that it allows a useful visualization of the three-dimensional data within the constraint of the two-dimensional computer display. This visualization is more like the two-dimensional pathological cutting image "slices" with which physicians are already familiar.

In a single two-dimensional projection, the underlying three-dimensional appearance of many objects is ambiguous. A spherically shaped object, such as a nodule, will appear as a circle in two-dimensional projection. However, a cylindrical object, such as a blood vessel, can also appear as a circle, if it is aligned perpendicular to the current two-dimensional projection. The spinning plane of the invention presents a multitude of views in a fast and comprehensible way, which allows the view to easily distinguish between scenarios that were initially ambiguous.

This "spinning plane" view is quite different than the typical volume rendering that many systems use to project three-dimensional data. These volume renderings require that a lot of decisions be made in advance as to what pixel values should appear transparent and what values should appear opaque or semi-opaque.

Figure 3:
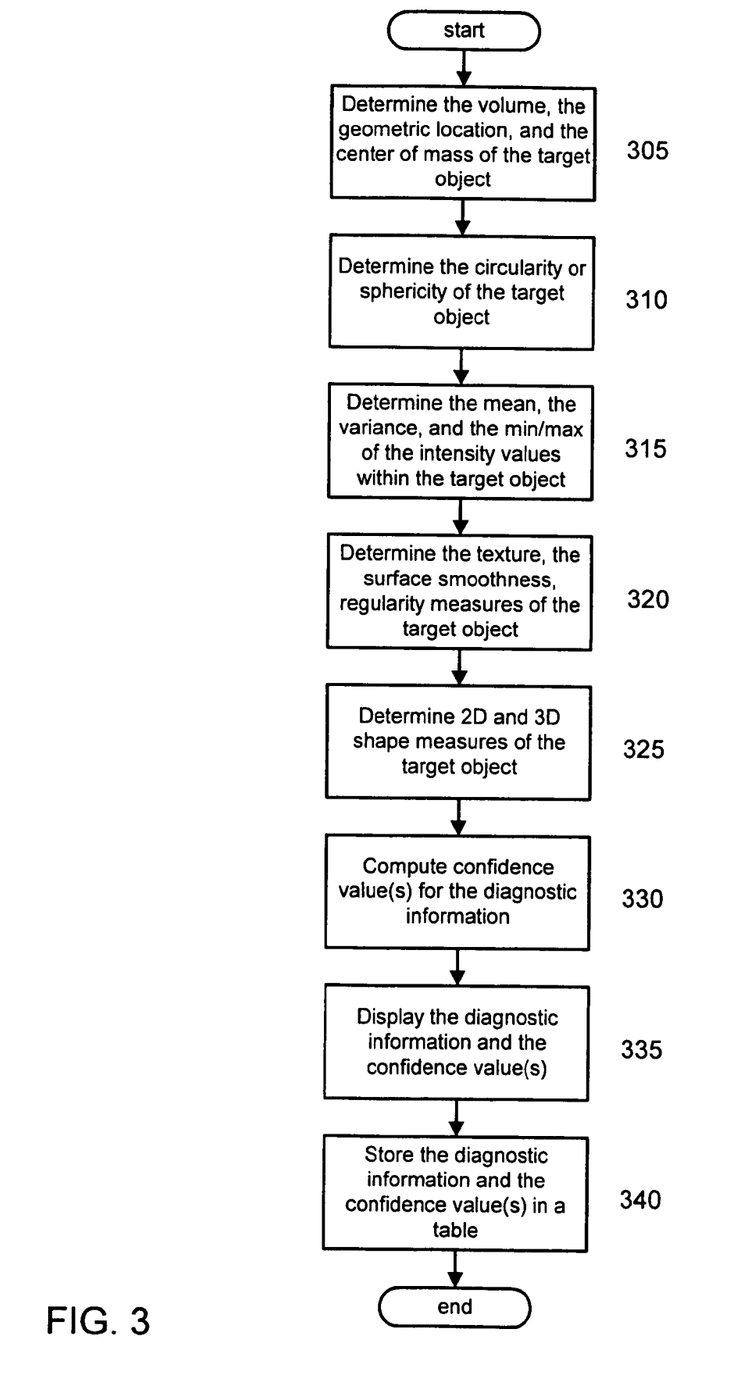
FIG. 3 is a flow diagram illustrating step 235 of FIG. 2 in further detail, according to an illustrative embodiment of the invention.

FIG. 3 is a flow diagram primarily illustrating step 235 of FIG. 2 in further detail, according to an illustrative embodiment of the invention. That is, most of the steps shown in FIG. 3 (the determining of diagnostic information) are performed during the spinning process described above, so that diagnostic information about the object for each of the different views in the spinning plane is automatically computed. The other steps of FIG. 3 may be performed during the spinning process or, preferably, subsequent thereto.

The volume, geometrical location, and center of mass of the target object are determined (step 305). The circularity or sphericity of the target object is determined (step 310). The mean, variance, and min/max of the intensity values within the target object are determined (step 315). The texture, the surface smoothness, and regularity measures of the target object are determined (step 320). Two-dimensional and three-dimensional shape measures of the target object are determined (step 325).

It is to be appreciated that the diagnostic information described with respect to steps 305–325 are merely illustrative of some of the diagnostic information which may be determined in accordance with the present invention. It is to be further appreciated that any combination or singular type of diagnostic information may be determined. Given the teachings of the present invention provided herein, one of ordinary skill in the related art will contemplate these and other types of diagnostic information, while maintaining the spirit and scope of the invention.

The computed diagnostic information gives rise to a confidence value(s), also stored in the table, describing an estimate of the clinical relevance of the object (step 330). Objects that are considered to be likely to be diseased will have a high confidence value. Other objects are that considered to be clinically significant, even if not indicative of actual disease, may also have a high confidence value. An example of the latter is a benign growth.

The computed diagnostic information of the target object and the associated confidence value(s) are displayed graphically to the physician (e.g., during or subsequent to the display of the cine loop or storage thereof) (step 335), and are then stored in a table for comparison with earlier or subsequent scans of the same patient (step 340). This comparison may be used for change detection in a patient who is being screened at some interval, or for monitoring progress in a patient undergoing treatment.

Upon request by the physician, the target object can be rendered using standard three-dimensional-volume visualization methods. This limited rendering of the target object by itself is less confusing and easier to interpret than a standard three-dimensional volume rendering of the entire volume data set, where other structures may block the view of the object.

Figure 4:
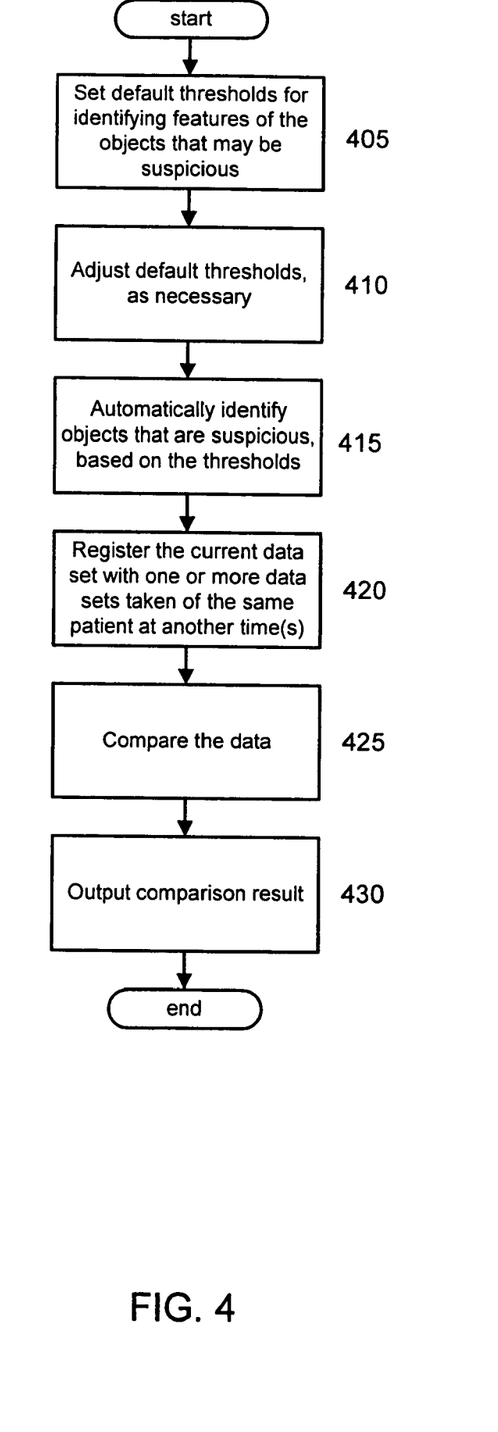
FIG. 4 is a flow diagram illustrating a method for suggesting candidate areas of suspicion, according to an illustrative embodiment of the invention.

FIG. 4 is a flow diagram illustrating a method for suggesting candidate areas of suspicion, according to an illustrative embodiment of the invention.

Based on the part of the body to be evaluated and the particular disease to be identified, thresholds are set for identifying features of objects that may be suspicious (step 405). These thresholds are set as default thresholds, which may be overridden and/or adjusted by a physician, as described below. Since these thresholds generally result from training of the system, and since they are used as default values, the thresholds are generally set prior to performing the method of FIG. 2.

Then, for each execution of the method of FIG. 2, the thresholds described above may be adjusted by the physician, as necessary (step 410). These adjustments may be made to meet individual preferences, or may be adjusted automatically in response to additional training data generated by physicians. These thresholds may also be adjusted to target a search for a particular disease or condition.

Next, objects are automatically identified as "suspicious", based upon the thresholds (either the default thresholds or the adjusted thresholds, if any) (step 415). Because computing object features over the entire data is time-consuming, the invention calculates the suspicious areas ahead of time, or in the background during the physician's manual inspection of the data.

When a large enough number of target objects have been identified, the current data set may be automatically registered with one or more data sets taken of the same patient at another time(s) (step 420). This registration will allow the system to directly compare the characteristics stored in the table (as described above) for a given object to be compared with characteristics of the same object at a different time (step 425). The comparison is presented to the physician so that the physician can monitor the patient for development of new disease, or for successful treatment of a detected disease (step 430).

Figure 5:
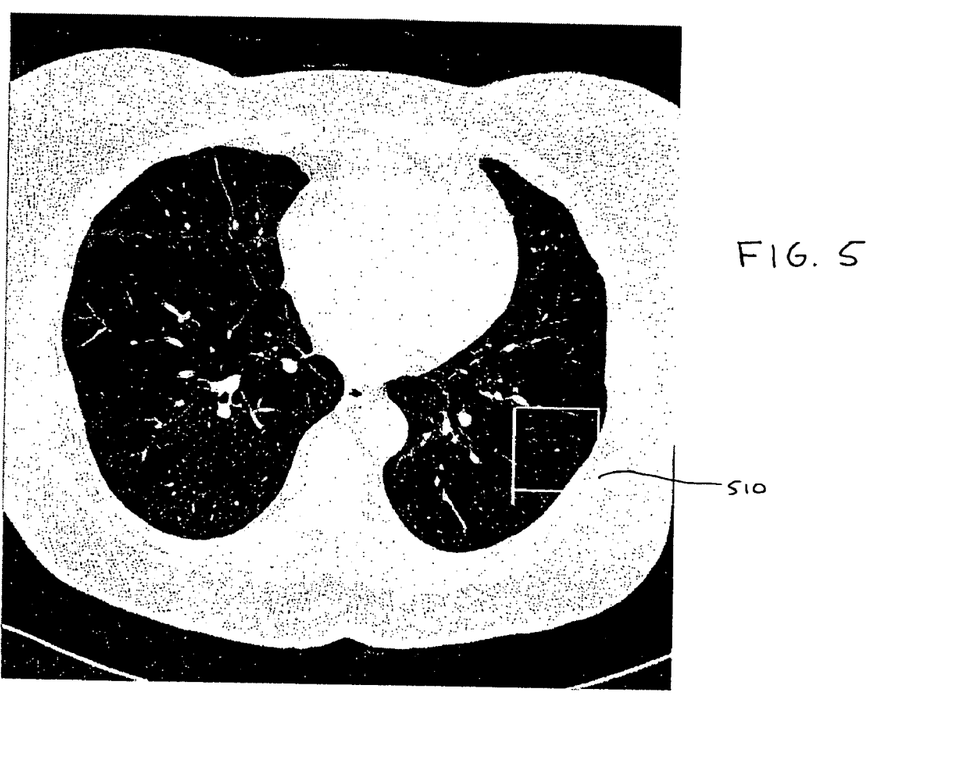
FIG. 5 illustrates a two-dimensional "slice" from a three-dimensional data set obtained by computed tomography (CT) of the lungs, according to an illustrative embodiment of the invention.

FIG. 5 illustrates a two-dimensional "slice" from a three-dimensional data set obtained by computed tomography (CT) of the lungs, according to an illustrative embodiment of the invention. The box 510 shows a region of interest (ROI), centered on a roughly circular area that looks "suspicious".

The circular area could correspond to a cross section of sphere or a cylinder. Spherical shapes are highly likely to be tumors, whereas cylindrical shapes generally correspond to branching blood vessels supplying blood to the lungs.

Figure 6:
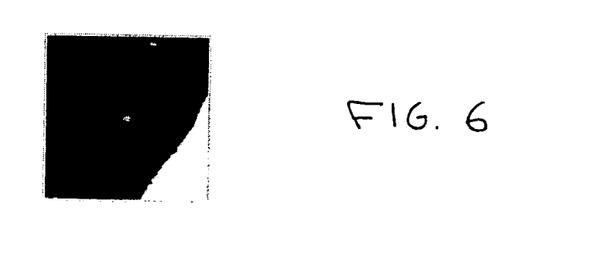
FIG. 6 is a magnified view of the region of interest (ROI) of FIG. 5, according to an illustrative embodiment of the invention.
Figure 7:
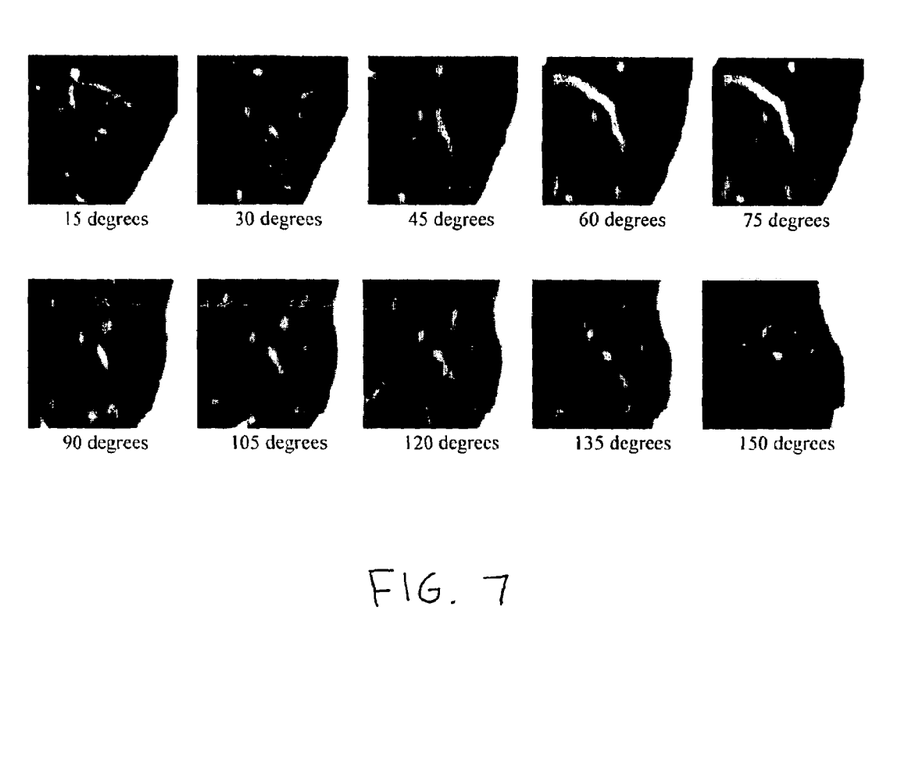
FIG. 7 illustrates frames from a "fly-around" movie, taken at 15 degree increments of the "spinning plane", according to an illustrative embodiment of the invention.

FIG. 6 is a magnified view of the region of interest (ROI) of FIG. 5, according to an illustrative embodiment of the invention. FIG. 7 illustrates frames from a "fly-around" movie, taken at 15 degree increments of the "spinning plane", according to an illustrative embodiment of the invention. As the angle approaches 60 degrees, it becomes obvious that the circular area in the center of FIG. 6 corresponds to a blood vessel and not a tumor.

Although the illustrative embodiments have been described herein with reference to the accompanying drawings, it is to be understood that the present system and method is not limited to those precise embodiments, and that various other changes and modifications may be affected therein by one skilled in the art without departing from the scope or spirit of the invention. All such changes and modifications are intended to be included within the scope of the invention as defined by the appended claims.

What is claimed is:

1. A computer-assisted diagnosis method for assisting diagnosis of three-dimensional digital medical image data, comprising the steps of:
   receiving indicia identifying at least one region of interest in a digital medical image; and
   identifying three-dimensional anatomical objects within the at least one region of interest;
   for a given three-dimensional anatomical object within the at least one region performing the following computer-implemented steps:
      determining an extent, a centroid, and a local spinning axis of the given anatomical object by examining connected voxels within a predefined volume on adjacent tomographic slices;
      determining a local spinning plane for the given anatomical object, the local spinning plane being centered at the centroid and the local spinning axis;
      rotating the local spinning plane at least a portion of 360 degrees, wherein said rotating step comprises the step of:
         automatically creating a view of the given anatomical object at computer selected increments of rotation, so as to result in a plurality of views of the given anatomical object at predefined angles in the rotation that are displayed in sequence as a cine loop.

2. The method according to claim 1, wherein the local spinning plane is initially oriented at a same angle as a current two-dimensional view of the three-dimensional digital medical image data.

3. The method according to claim 1, wherein said step of providing the plurality of views of the given anatomical object further comprises the step of providing a plurality of views of areas surrounding the given anatomical object.

4. The method according to claim 1, wherein the indicia is provided from a user through one of a mouse and an eye tracking device.

5. The method according to claim 1, wherein said providing step further comprises the step of determining at least one of a volume, a geometrical location, and a center of mass of the given anatomical object.

6. The method according to claim 1, wherein said providing step further comprises the step of determining one of a circularity and a sphericity of the given anatomical object.

7. The method according to claim 1, wherein said providing step further comprises the step of determining a mean, a variance, and a min/max of intensity values within the given anatomical object.

8. The method according to claim 1, wherein said providing step further comprises the step of determining a texture, a surface smoothness, and regularity measures of the given object.

9. The method according to claim 1, wherein said providing step further comprises the step of determining two-dimensional and three-dimensional shape measures of the given anatomical object.

10. The method according to claim 1, further comprising the step of storing results from said providing step in a table for comparison with at least one of preceding or succeeding scans of a same patient.

11. The method according to claim 10, further comprising the step of storing a confidence value in the table that indicates an estimate of a clinical relevance of the given anatomical object.

12. The method according to claim 1, further comprising the steps of:
   setting thresholds for particular features of particular anatomical objects that represent whether the particular anatomical objects are abnormal; and
   identifying a given anatomical object that exceeds a given threshold.

13. A program storage device readable by machine, tangibly embodying a program of instructions executable by the machine to perform steps for computer-assisted diagnosis of three-dimensional digital medical image data, said method steps comprising:
   receiving indicia identifying at least one region of interest in a digital medical image; and
   identifying three-dimensional anatomical objects within the at least one region of interest;
   for a given three-dimensional anatomical object within the at least one region performing the following computer implemented steps:
   determining an extent a centroid, and a local spinning axis of the given anatomical object by examining connected voxels within a predefined volume on adjacent tomographic slices;
   determining a local spinning plane for the given anatomical object, the local spinning plane being centered at the centroid and the local spinning axis;
   rotating the local spinning plane at least a portion of 360 degrees, wherein said rotating step comprises the step of:
   automatically creating a view of the given anatomical object at computer selected increments of rotation, so as to result in a plurality of views of the given anatomical object at predefined angles in the rotation that are displayed in sequence as a cine loop.

14. The program storage device according to claim 13, wherein the local spinning plane is initially oriented at a same angle as a current two-dimensional view of the three-dimensional digital medical image data.

15. The program storage device according to claim 13, wherein said step of providing the plurality of views of the given anatomical object further comprises the step of providing a plurality of views of areas surrounding the given anatomical object.

16. The program storage device according to claim 13, wherein the indicia is provided from a user through one of a mouse and an eye tracking device.

17. The program storage device according to claim 13, wherein said providing step further comprises the step of determining at least one of a volume, a geometrical location, and a center of mass of the given anatomical object.

18. The program storage device according to claim 13, wherein said providing step further comprises the step of determining one of a circularity and a sphericity of the given anatomical object.

19. The program storage device according to claim 13, wherein said providing step further comprises the step of determining a mean, a variance, and a min/max of intensity values within the given anatomical object.

20. The program storage device according to claim 13, wherein said providing step further comprises the step of determining a texture, a surface smoothness, and regularity measures of the given anatomical object.

21. The program storage device according to claim 13, wherein said providing step further comprises the step of determining two-dimensional and three-dimensional shape measures of the given anatomical object.

22. The program storage device according to claim 13, further comprising the step of storing results from said providing step in a table for comparison with at least one of preceding or succeeding scans of a same patient.

23. The program storage device according to claim 22, further comprising the step of storing a confidence value in the table that indicates an estimate of a clinical relevance of the given anatomical object.

24. The program storage device according to claim 13, further comprising the steps of:
- setting thresholds for particular features of particular anatomical objects that represent whether the particular anatomical objects are abnormal; and
- identifying a given anatomical object that exceeds a given threshold.

* * * * *

UNITED STATES PATENT AND TRADEMARK OFFICE
CERTIFICATE OF CORRECTION

PATENT NO. : 6,983,063 B1  Page 1 of 1
DATED : August 30, 2005
INVENTOR(S) : Miodrag Temerinac It is certified that error appears in the above-identified patent and that said Letters Patent is hereby corrected as shown below:

<u>Column 6,</u>
Line 10, before "dashed" delete "at".
Line 42, delete "$C_{N=1}$" and insert -- $C_{N-1}$ --.

Signed and Sealed this

First Day of November, 2005

JON W. DUDAS
*Director of the United States Patent and Trademark Office*